United States Patent [19]

Lansel

[11] Patent Number: 4,792,332
[45] Date of Patent: Dec. 20, 1988

[54] APPARATUS FOR COLONIC IRRIGATION

[76] Inventor: Toby Lansel, 4125 East Pender Street, Burnaby, British Columbia, Canada, V5C 2M2

[21] Appl. No.: 17,984

[22] Filed: Feb. 24, 1987

[51] Int. Cl.$^4$ .............................................. A61M 3/00
[52] U.S. Cl. ...................................... 604/276; 4/420; 128/DIG. 26
[58] Field of Search ............... 604/275, 276, 277, 279, 604/39, 41, 42; 128/DIG. 26; 4/420, 420.1–420.5, 443, 445

[56] References Cited

U.S. PATENT DOCUMENTS

| | | | |
|---|---|---|---|
| 2,818,862 | 1/1958 | Wanek | 604/276 |
| 2,852,025 | 9/1958 | Wessels | 604/276 |
| 4,321,920 | 3/1982 | Gillig | 604/275 |
| 4,453,933 | 6/1984 | Speaker | 128/DIG. 26 |
| 4,480,639 | 11/1984 | Peterson et al. | 128/DIG. 26 |
| 4,606,735 | 8/1986 | Wilder et al. | 128/DIg. 26 |
| 4,645,497 | 2/1987 | Lowder | 604/276 |

FOREIGN PATENT DOCUMENTS 0594746  3/1934  Fed. Rep. of Germany ...... 604/275

Primary Examiner—Dalton L. Truluck
Assistant Examiner—F. Wilkens
Attorney, Agent, or Firm—Fetherstonhaugh & Co.

[57] ABSTRACT

A user operated colonic irrigaiton device. The device comprising a board to be received on a lavatory and to receive a person undergoing treatment with a generally triangular opening in the board. A resilient hood with an open end, being resiliently deformable to fit within the opening in the board and tapering from the open end to the closed end to match the shape of the generally triangular opening. The hood can be located in the opening by recesses on each side of the hood, able to engage the board. An abutment on the exterior of the closed end of the hood contacts the upper surface of the board. A tube is able to communicate a supply of liquid to the person. The tube is supported by a bracket extending upwardly from the hood. There is a recess in the bracket able to releasably grip the tube. The board is easy to clean and sterilize, relatively inexpensive to manufacture and more simple and practical than prior art boards.

1 Claim, 2 Drawing Sheets

U.S. Patent   Dec. 20, 1988   Sheet 1 of 2   4,792,332
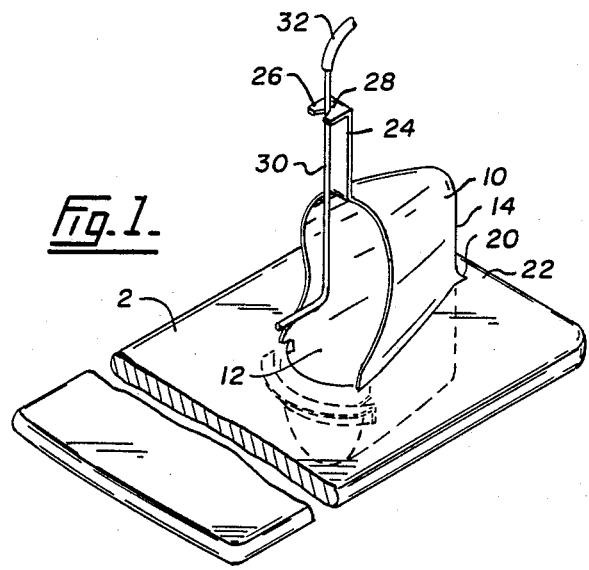
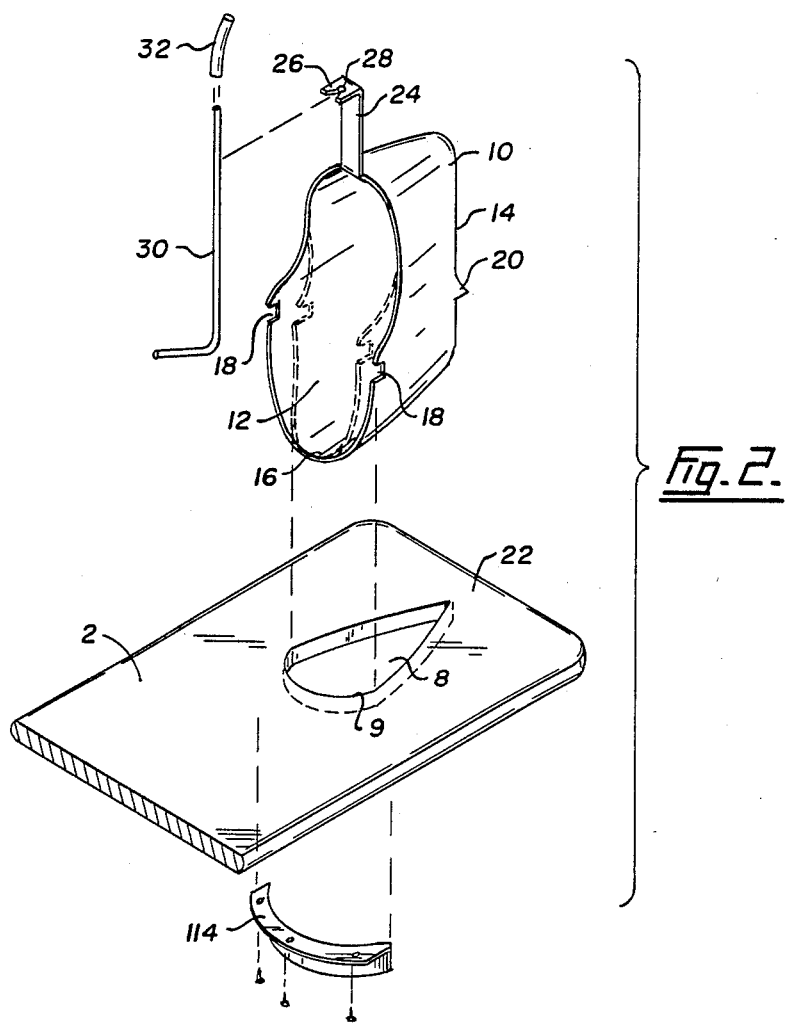

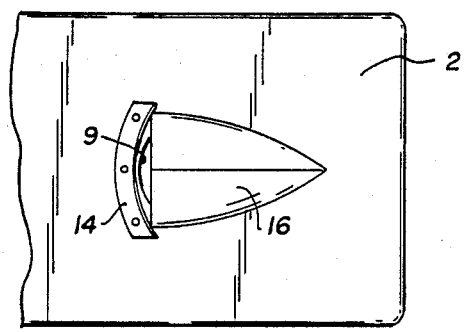
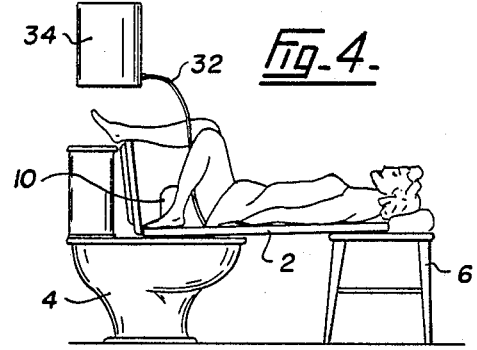

4,792,332

APPARATUS FOR COLONIC IRRIGATION

FIELD OF THE INVENTION

This invention relates to a user operated device for colonic irrigation.

DESCRIPTION OF THE PRIOR ART

Colonic irrigation is a method of cleansing the colon thoroughly. It is carried out by the insertion of a liquid into the colon, through a tube. The resemblance to the administration of an enema is obvious but, generally, the procedure in colonic irrigation differs by leaving the rectal tube in place during evacuation. In using the colonic irrigation board the board is placed over a lavatory with one end remote from the lavatory, supported by a chair or the like. The person to receive treatment lies on the board, on his or her back. A rectal tube is inserted and fluid flow started. The was fluid passes out of the rectum and is directed by a hood through an opening in the board to the lavatory.

There are presently a number of colonic irrigation devices on the market. In such prior art boards the rectal tube typically extends from within the hood. This relatively inflexible means of mounting the tube means that the person using the colonic board has to ease down on the rectal tube for insertion. This can be awkward. The ideal rectal tube should prevent insertion more than three inches in order to avoid risk of injury. It should also be hand operated during insertion and removal while automatically held in position during the procedure allowing limited movements of the torso of the user without unintentional removal or risk of injury and allow the person using the device to have both hands free to control fluid supply and massage the abdomen.

Ease of cleaning and sterilization are highly desirable features for this kind of equipment and also that backsplash and splashing from the toilet on the underside of the board be eliminated. It is also desirable that inexpensive methods of manufacturing such as plastic molding can be utilized.

SUMMARY OF THE INVENTION

The present invention seeks to provide a simple apparatus fulfilling all these requirements.

Accordingly the present invention is a colonic irrigation board comprising a board to be received on a lavatory and to receive a person undergoing treatment; a generally triangular opening in the board; a resilient hood having an open front end, the hood being resiliently deformable to fit within the opening in the board and tapering from the open front end to the close back end to match the shape of the generally triangular opening; means to locate the hood in the opening comprising recesses on each side of the hood, and able to engage the board; an abutment on the exterior of the closed end of the hood to contact the upper surface of the board; means to receive a tube able to communicate a supply of liquid to the user, said means comprising a bracket extending upwardly from the hood a recess in the bracket able to releasably and slideably grip the tube in a way that leaves its lower end moveable in all directions.

BRIEF DESCRIPTION OF THE DRAWINGS

Aspects of the invention are illustrated, merely by way of example, in the accompanying drawings in which:

FIG. 1 is an isometric view of an embodiment of the invention;

FIG. 2 is an exploded view of the embodiment of FIG. 1;

FIG. 3 shows the underside of the board with the hood mounted;

FIG. 4 is a general view showing use of the apparatus; and

DESCRIPTION OF THE PREFERRED EMBODIMENTS

FIGS. 1 and 2 show an apparatus comprising a board 2 to be received, for example, on a lavatory 4 and supported by a stool 6, see FIG. 4. The board 2 has an opening 8 alignable with the lavatory bowl top. Opening 8 is generally triangular with its forward edge 9 curved and extending outwardly to its centre as shown most clearly in FIG. 2. On the underside of the board and adjacent to the curved edge 9 there is an abutment 114 that prevents any possibility of spray on the front rim of the toilet.

There is a resilient hood 10 having an open front end 12 tapering to a closed back end 14 and with an closed base 16. The hood 10 is formed of any suitable resilient material, for example high density polyethylene, so that it may be compressed, inserted into the opening 8 then allowed to resile outwardly to assume the position shown in FIG. 1. The compressed position is shown in broken lines in FIG. 2. To locate the hood 10 in the board 2 the hood 10 is provided with recesses 18. Further there is an abutment 20 extending from the closed back end of the hood 10 to contact the upper surface of the board at 22.

The hood 10 has a bracket 24 extending upwardly. The bracket 24 has a limb 26 with a recess 28, widening outwardly. A tube 30 is received in recess 28. The tube 30 is a press-fit in recess 28.

Tube 30 is generally L-shaped and extends downwardly then forwardly of the hood. In use the upper end is connected to, for example, a rubber tube 32 connected to a supply of fluid 34, see FIG. 4.

To set up the apparatus of FIGS. 1 and 2 board 2 is placed in a desired position, for example, on a lavatory top as shown in FIG. 4 with the abutment 114 inside the toilet bowl. Hood 10 is compressed by hand and inserted through the opening 8. The generally triangular shape of opening 8 and, particularly, the outwardly curved shape of the front edge 9 of opening 8 help positioning of the hood within the opening. Once in position hood 10 is released and the sides resile outwardly so that the recesses 18 engage the board as shown particularly in FIG. 1 with abutment 20 contacting board 2 at 22.

Before lying on the board 2 the user clips tube 30 into recess 28 in limb 26 of bracket 24. The lower end of tube 30 is lubricated. The user lies on the board, as shown in FIG. 4. The tube 30 is snapped out of recess 28, the end is inserted into the rectum then the tube is snapped back into recess 28. Water flow is started and usually is controlled by the user.

The support of the tube 30 in the recess 28 and at tee lower end of bracket 24 prevents the tube from unintentional removal during the procedure and because tube 30 is vertically slideable in recess 28 individual fit is assured. Furthermore, the moveable lower end of the tube allows mmovements of the torso of the user. This is considered of extreme importance. If the tube 30 is rigidly held in place during movements by the user it could injure the rectal wall.

Tube 30 is generally a slide fit within recess 28 but the presence of tube 32, connected to fluid supply 34, prevents the tube 30 moving too far and thus slipping out of recess 28.

The closed base 16 prevents splashing on the underside of the board from the toilet. The abutment 114 prevents any possibility of spray on the front rim of the toilet bowl while in use, thus ensuring that all waste water and material be directed into the toilet in a smooth way.

The present invention has the virtue of ease of use. Further the triangular or tapered shape of the hood greatly reduces splashing. Furthermore after use the cleaning and sterilization of the apparatus is a simple matter because the apparatus is very easy to dismantle.

The board 2 may desirably be of wood or formed of a plastic material. Smooth surfaces, to facilitate cleaning, are important. As indicated the hood 10 is desirably of a high density polyethylene but any resilient plastic material, robust enough to be used frequently is suitable. Similarly the tube 30 is desirably of plastic material with high resistance to breaking.

It should also be noted that compared with other colonic irrigation devices the production of the present invention is relatively inexpensive, because plastic molding is a suitable method of manufacturing of the different components of the device.

I claim:

1. A user operated device for colonic irrigation comprising:
    a board to be received on a lavatory and to receive a person undergoing treatment, said board having a generally triangular opening with an outwardly curved base;
    a resilient hood having only the front open, the hood being removably connected to said board by virtue of said hood being resiliently deformable to fit within the opening in the board, said hood tapering form the open front end to the closed back end to match the shape of the generally triangular opening, said hood having a section extending below forming an exit opening therethrough;
    means to locate the hood in the opening comprising recesses on each side of the hood, and able to engage the board;
    an abutment on the exterior of the closed back end of the hood to contact the upper surface of the board;
    a bracket extending upwardly from the hood to receive an L-shaped tube able to communicate a supply of liquid to the user;
    a recess in the distal end of the bracket able to releasably and slideably grip the tube in a way that leaves lower end of the tube moveable in all directions except that said tube is being restricted in its movement towards the hood because of contact with the base of said bracket;
    an abutment on the underside of the board, adjacent the outwardly curved base of the generally triangular opening.

* * * * *